US011351419B2

United States Patent
Loh et al.

(10) Patent No.: US 11,351,419 B2
(45) Date of Patent: Jun. 7, 2022

(54) SMART GYM

(71) Applicant: INTEL CORPORATION, Santa Clara, CA (US)

(72) Inventors: Sean Yit Loh, Bayan Lepas (MY); Yoke Ming Tan, Gelugor (MY); Michelle Ching Yee Lim, Tanjung Tokong (MY); Woon Soon Wong, Seremban (MY); Wei Th'ng Yew, Jelutong (MY); Cheah Cheat Lee, Butterworth (MY)

(73) Assignee: INTEL CORPORATION

( * ) Notice: Subject to any disclaimer, the term of this patent is extended or adjusted under 35 U.S.C. 154(b) by 286 days.

(21) Appl. No.: 16/720,775

(22) Filed: Dec. 19, 2019

(65) Prior Publication Data

US 2020/0121987 A1 Apr. 23, 2020

(51) Int. Cl.
*A63B 24/00* (2006.01)

(52) U.S. Cl.
CPC ...... *A63B 24/0062* (2013.01); *A63B 24/0075* (2013.01); *A63B 2230/01* (2013.01); *A63B 2230/75* (2013.01)

(58) Field of Classification Search
CPC ............ A63B 24/0062; A63B 24/0075; A63B 2230/01; A63B 2230/75; A61B 5/0077; A61B 5/6892; A61B 2503/10; A61B 5/6895; A61B 5/1118; A61B 5/1123; A61B 2562/0247; A61B 5/1128; G06K 9/00342

See application file for complete search history.

(56) References Cited

U.S. PATENT DOCUMENTS

| | | | |
|---|---|---|---|
| 10,078,795 B2* | 9/2018 | Tao | G06T 7/20 |
| 10,931,880 B2* | 2/2021 | Byeon | A63B 71/0622 |
| 10,960,266 B2* | 3/2021 | Messinger | G06N 5/04 |
| 11,004,356 B2* | 5/2021 | Kato | G09B 19/0038 |
| 2011/0251493 A1* | 10/2011 | Poh | G06K 9/624 600/477 |
| 2012/0268592 A1* | 10/2012 | Aragones | G09B 19/0038 348/143 |
| 2014/0267611 A1* | 9/2014 | Kennett | G06K 9/00335 348/46 |
| 2016/0042529 A1* | 2/2016 | Tao | G06K 9/6202 382/107 |
| 2017/0056715 A1* | 3/2017 | Dalebout | A63B 23/1236 |
| 2017/0368413 A1* | 12/2017 | Shavit | G06K 9/00342 |
| 2018/0064992 A1* | 3/2018 | Rothman | A63B 21/00181 |

(Continued)

OTHER PUBLICATIONS

Spice, Byron: "A Computer that Reads body Language", Jul. 6, 2017 Carnegie Mellon University, retrieved from the internet; https://www.es.cmu.edu/news/computer-reads-body-language, 4 pages.

(Continued)

*Primary Examiner* — Sundhara M Ganesan
(74) *Attorney, Agent, or Firm* — Hanley, Flight & Zimmerman, LLC (57) ABSTRACT

An apparatus for a smart gym is described herein. The smart gym includes a platform and at least one camera. The platform comprises at least a weight sensor. The at least one camera is configured to capture movements on the platform. In some cases, an exercise is identified by comparing the joint movement to a known joint movement associated with the exercise.

25 Claims, 6 Drawing Sheets

(56) References Cited

U.S. PATENT DOCUMENTS

2020/0009444 A1* 1/2020 Putnam .............. A63B 24/0062
2020/0020165 A1* 1/2020 Tran ....................... G06N 7/005
2021/0197022 A1* 7/2021 Liu ........................ G16H 40/67
2021/0335474 A1* 10/2021 Harma ............... A63B 24/0087

OTHER PUBLICATIONS

Quinn, Elizabeth: "Using Metabolic Equivalent for Task (MET) for Exercises", updated Sep. 19, 2019, retrieved form the internet: https://www.verywellfit.com/met-the-standard-metabolic-equivalent-3120356, 3pages.

Waehner, Paige: "How to Calculate the Calories You Burn During Exercise", updated Sep. 29, 2019, retrieved form the internet: https://www.verywellfit.com/how-many-calories-you-burn-during-exercise-4111064, 4 pages.

PROCON.Org: "MET Values for 800+ Activities", updated Mar. 11, 2019, retrieved form the internet: https://golf.procon.org/met-values-for-800-activities, 67 pages.

Stein, Sydney: "How Many Calories Are Burned During 30 Minutes of Weight Lifting?" updated Aug. 13, 2019, retrieved from the internet, https://www.livestrong.com/article/228804-how-many-calories-are-burned-during-30-minutes-of-weight-lifting/#ixzz1yihyolmn, 2 pages.

Robinson, Allan, "Calories Burned From High-Intensity Interval Training", updated Jan. 5, 2018, retrieved from the internet, https://www.livestrong.com/article/228774-calories-burned from-high-intensity-interval-training/, 2 pages.

\* cited by examiner

SMART GYM

BACKGROUND

Fitness or activity trackers are common devices that can be integrated into a number of wearables. For example, the trackers may be components of smart watch devices. Devices that include trackers can monitor a user's physical activity as well as biometric data. For example, a fitness tracker may calculate a person's steps and movement throughout the day. This data may then be used to determine the person's caloric expenditure for a particular length of time.

The same numbers are used throughout the disclosure and the figures to reference like components and features. Numbers in the 100 series refer to features originally found in FIG. 1; numbers in the 200 series refer to features originally found in FIG. 2B; and so on.

DESCRIPTION OF THE EMBODIMENTS

As discussed above, traditional fitness or activity trackers are commonly integrated into wearable devices, such as smart watches. Data captured by a fitness tracker can be used to calculate a caloric expenditure for a person. A caloric expenditure may refer to a number of calories burned by a person during a particular time window. To accurately calculate caloric expenditures, traditional fitness trackers use exercise profiles. An exercise profile may indicate the particular activity to be performed. By having beforehand knowledge of an activity to be performed by a user, a fitness tracker can more accurately calculate the caloric expenditures of a user. Exercise profiles may include, for example, swimming, running and high intensity interval training (HIIT).

Exercise profiles are limited to monitoring a wearer's biometric information, such as heart rate. As such, traditional fitness trackers lack the functionality to track free weight exercise or floor exercises. Free weight exercises are movements that are performed with free weights, as opposed to machine weights. Free weight exercises apply additional weight to muscles of the body while moving or configuring the body in and out of a skeletal configuration. Floor exercises, as used herein, refer to exercises that require the human body to achieve a skeletal configuration with the goal of stressing muscles in that configuration. This may be referred to as free-form exercises.

Traditional fitness trackers cannot accurately track total body movement for exercises such as free-weight exercises and floor exercises. While some traditional trackers can account for movement from a single point of reference, the traditional trackers cannot track the entire movement associated with moving in and out of a skeletal configuration. For example, the movement for doing a weighted barbell squat can be relatively small as detected by fitness tracker worn at a single point. Thus, a tracker based on movement will only detect a small movement. However, but the actual calories burnt during an entire weighted barbell squat can be significantly higher due to the weight added to the barbell. This inaccurate tracking of free weights and floor exercise can render traditional trackers useless, as free weight exercises and floor exercises are integral to a complete fitness routine. Thus, the inability to accurately track floor exercises leaves a void in interactive fitness. Traditional fitness trackers are also unable to track calories burnt and repetition counting for dumbbell weights and weight lifting.

The present techniques enable a smart gym. As described herein, the smart gym enables an accurate calorie expenditure calculation when performing exercises. In particular, the present techniques enable an accurate calorie expenditure calculation when tracking free weight exercises or floor exercises. Parameters such as skeletal movements and the weight held during the skeletal movements may be tracked via a plurality of sensors. The sensor may include image sensors and weight sensors. Fitness data, including a calorie expenditure, may be derived from the parameters. Additionally, repetitions of the free weights may be counted for the free weight exercise or floor exercises. In embodiments, the present techniques enable virtual coaching. For example, the smart gym enables tracking during free weight exercise or floor exercises as a training aid for professional athletes and coaches. The fitness data may be shared, in real time, with coaches or other professionals who can provide coaching based on the derived fitness data. Additionally, in embodiments, the present techniques enable augmented-reality applications for users who want to virtually train with public figures, such as a favorite athlete or celebrity.

Figure 1:
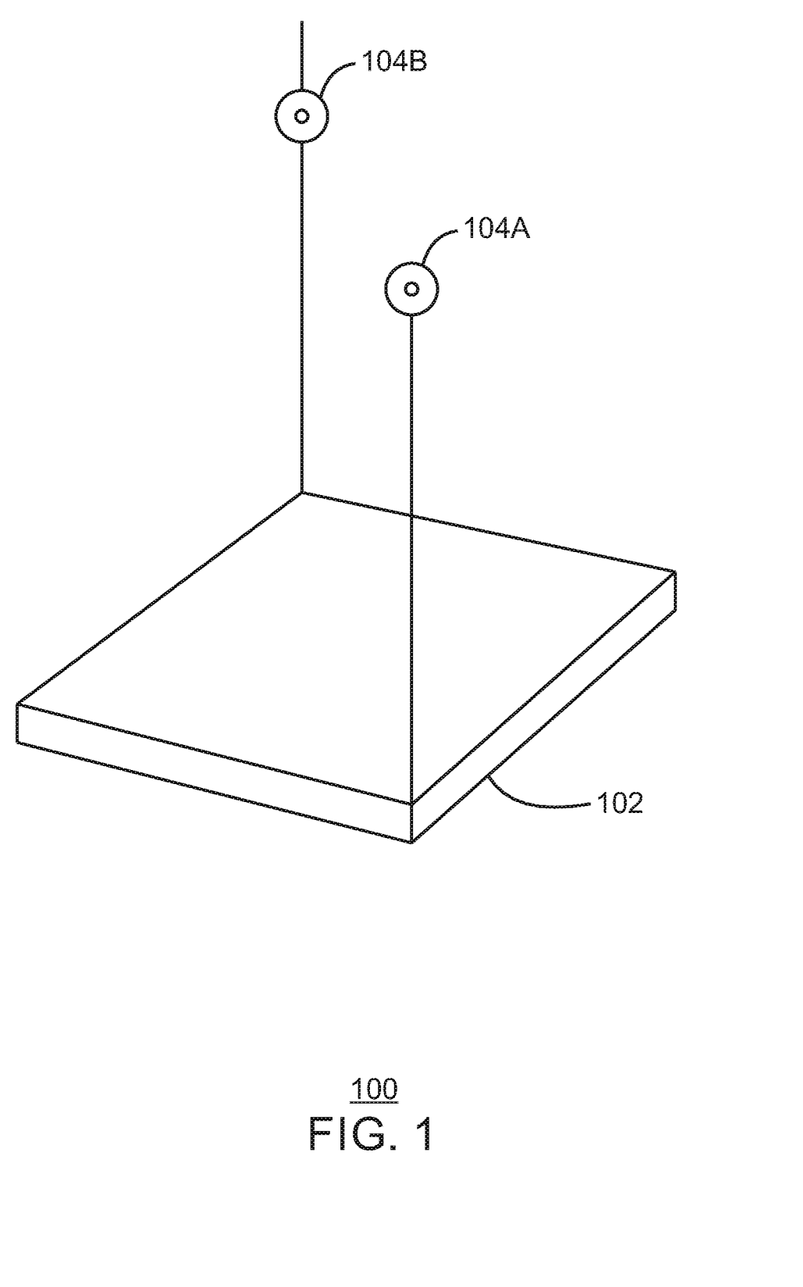
FIG. 1 is a block diagram of a smart gym.

FIG. 1 is a block diagram of a smart gym 100. The smart gym 100 includes a base 102 and one or more cameras 104. In the example of FIG. 1, two cameras 104A and 104B are illustrated in the smart gym 100. The base 100 may a platform with a number of sensors embedded in the platform. Thus, the platform may include a number of sensors to capture the weight of one or more users on the platform. In embodiments, the platform is a weight scale or a plurality of weight scales with designated workout areas for one or more users. The platform may include markings such as lines, circles, or any combination thereof to indicate one or more workout areas. Thus, the platform may designate a workout area for one or more users, where all free weight exercise or floor exercises are performed on the platform within the workout area. As illustrated, the two cameras 104A and 104B are located above the workout area in opposing corners to capture a person engaging in free weight exercise or floor exercises. In embodiments, the cameras are wide angle cameras that can capture the entire workout areas with a wide angle. The cameras may capture movements made by a person while within the workout area.

Images captured by the cameras 104A and 104B may be used to extract a skeleton frame that represents the person. The various points on the skeleton frame may be analyzed to identify and track particular joint movements executed by the person. In embodiments, a processing unit, such as a vision processing unit (VPU) or a graphics processing unit (GPU), may be used to extract the skeleton frame of the person and identify and track the particular movements executed by the person. In embodiments, the processing unit may include a neural compute engine that is a dedicated hardware accelerator for deep neural network deep-learning inferences. Configurations of the skeleton frame can be used to train on-device deep neural networks and computer vision applications executed by the VPU. Additionally, the configurations of the skeleton frame can be analyzed to compute calorie calculation.

Figure 2:
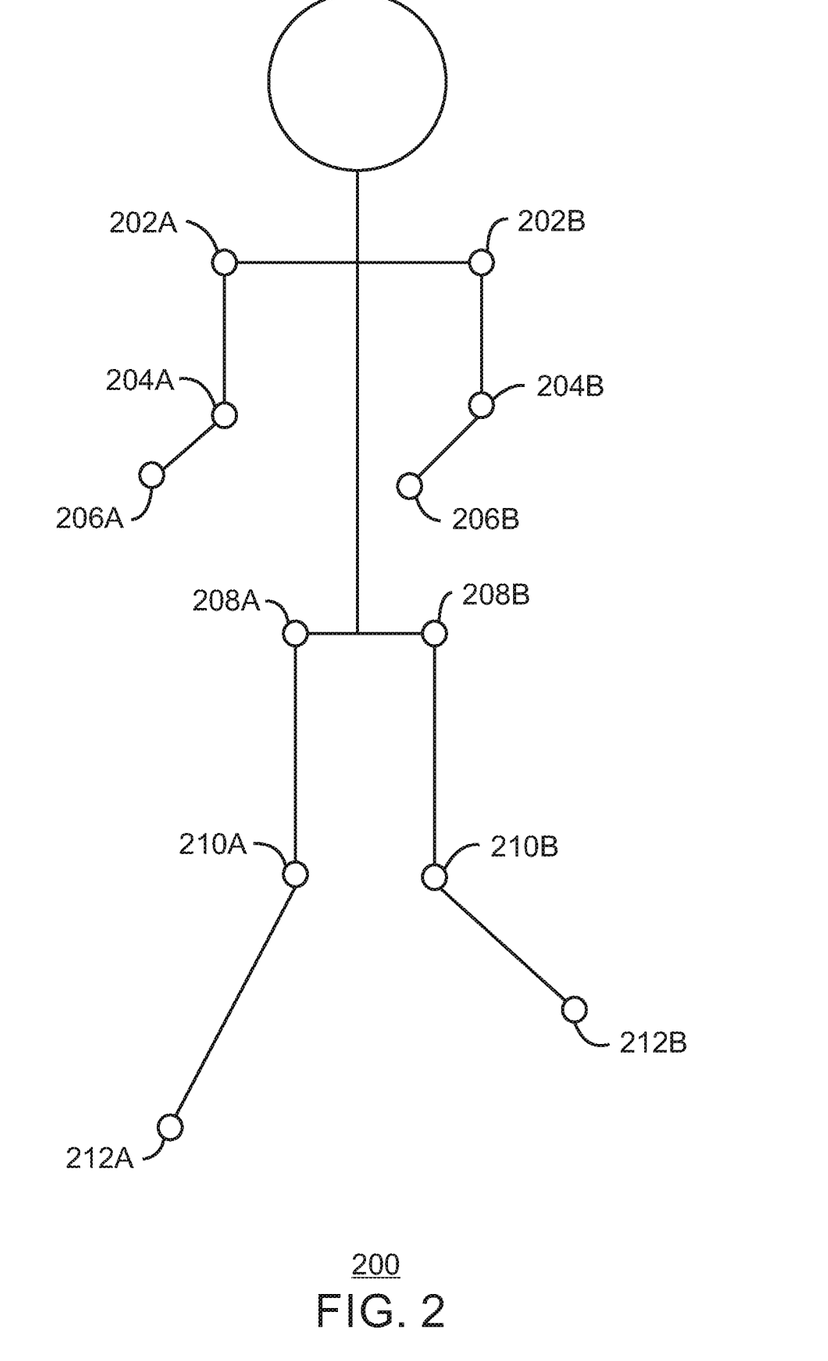
FIG. 2 is a skeleton frame.

FIG. 2 is a skeleton frame 200. The skeleton frame may be extracted from a plurality of images captured by cameras in a smart gym. In embodiments, the skeleton frame is extracted as a set of joints. As illustrated in FIG. 2, the skeleton frame 200 has a total of 12 joints. Configurations that result from movement of the skeleton frame 200 may be tracked according to the movement of each joint 202A, 202B, 204A, 204B, 206A, 206B, 208A, 208B, 210A, 210B, 212A, and 212B. As illustrated, joint 202A is a right shoulder joint, and joint 202B is a left shoulder joint. Joint 204A is a right elbow joint, and joint 204B is a left elbow joint. Joint 206A is a right wrist joint, and joint 206B is a left wrist joint. Joint 208A is a right hip joint, and joint 208B is a left hip joint. Joint 210A is a right knee joint, and joint 2108 is a left knee joint. Joint 212A is a right ankle joint, and joint 2128 is a left ankle joint. For ease of description, a particular set of joints are illustrated. However, any number of joints may be found along the human skeleton. Additionally, any movement possible with the human skeleton associated with one or more joints that can be tracked according to the present techniques.

The particular movement possible may be defined by the type of joint. The movements include, but are not limited to angular movements, such as flexion and extension, abduction, adduction, circumduction, rotation, medial rotation, lateral rotation, external rotation, internal rotation, inversion, eversion, protraction, retraction, elevation, depression, opposition, supination, pronation, or any combinations thereof. Additionally, abnormal joint movements may be hyperextension, hyperflexion.

The diagram of FIG. 2 is not intended to indicate that the example skeleton frame 200 is to include all of the joints shown in FIG. 2. Rather, the example system 200 can be implemented using fewer or additional components not illustrated in FIG. 2 (e.g., additional joints, other skeleton frame points, etc.) For example, the neck may serve as an additional joint location on the skeleton frame. Moreover, a series of points or a line representing the spine of the person may serve as another skeleton frame point that may be tracked.

In embodiments, cameras of the smart gym may be used to pin-point the 12 points (joints) to derive along the skeleton frame for movement identification. In embodiments, the captured images and derived skeleton frame information may be captured and stored in the cloud. Accordingly, the smart gym is a cloud storage solution that is used to store the personal information, exercise activity logs, duration of exercise, and the calories burned for a person.

In embodiments, movements of the skeleton frame are combined with other sensor data. For example, the platform may include weight sensors. A user may scan-in to begin free weight exercise or floor exercises. During the scan-in process, an initial user weight may be captured. After the scan-in, the weight sensors of the platform may be used to capture the weight of any accessories used by the user during the workout. For example, if the user picks up barbells to begin a free weight exercise, the platform can capture the total weight of the user, which will be increased by the weight of the barbells when compared to the weight of the user during the scan-in. The weight of the user during exercise may be captured simultaneously with the images of the user at a processing unit.

Figure 3:
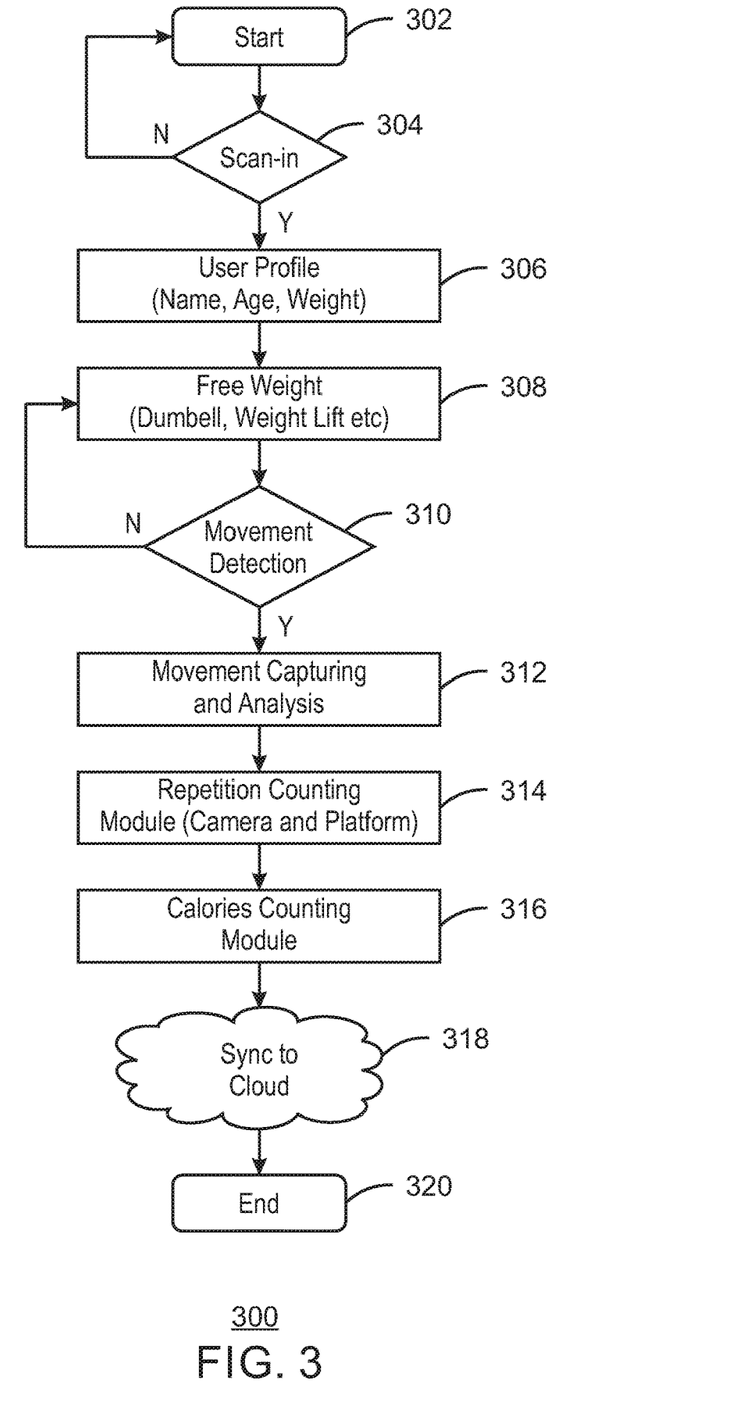
FIG. 3 is a process flow diagram of a method that enables a smart gym.

FIG. 3 is a process flow diagram of a method 300 that enables a smart gym. The example method 300 can be implemented in the systems 400 of FIG. 4, the computing device 500 of FIG. 5, or the computer readable media 600 of FIG. 6. For example, the method 300 can be implemented using the processing unit 406, CPU 502, VPU/GPU 508, or the processor 602. At block 302, the method begins. At block 304, it is determined if a user is scanned in. If the user is scanned in, process flow continues to block 306. If the user is not scanned in, process flow returns to block 302 where the method starts and the user is pulled until the user is scanned in. During a scan-in, the profile information of the user is obtained from the user or a data store. Accordingly, at block 306, a user profile is obtained. The user profile may include user identifications or identifiers such as name, age, and weight. The user profile may also include other information used to calculate a calorie expenditure, such as sex, height, and the like.

At block 308, the particular free weight, if any, being used in an exercise by the user is determined. The free weight may be determined from an image captured via cameras in the smart gym. The free weight may also be determined according to a weight difference of the user when compared to the original weight of the user during the scan-in process. At block 310, the workout area is monitored to detect movement. The movement detected may be the movement of a user in and out of a particular skeletal configuration. If movement of the user is detected, the process flow continues to block 312. If movement is not detected, process flow returns to block 308 where the present techniques scan for the particular weight held by the user. At block 312, movement capturing and analysis occurs. During movement capture and analysis, the movements of the skeleton frame of a user can be extracted by tracking the plurality of joints captured by images of the user. The movement capture may also capture movement of the user as far as jumping, sidestepping, and other movements that may move the entire skeleton frame within the workout area of the platform with little to no joint movement. Simultaneously, the weights used by the user during the movement are also captured by the cameras (image sensors) of the smart gym or by weight sensors in a platform of the smart gym. In this manner, the smart gym is able to extract the particular movements executed by the user and the weights used by the user during exercise.

At block 314, a repetition counting module is executed. The repetition counting module will count a number of repetitions that a user successfully completes of an exercise. As used here in, a repetition (rep) is defined as a complete movement that counts as one instance of a particular exercise. In embodiments, exercises may be defined by known joint movements for each joint during the exercise. A repetition of an exercise may be complete once the joints of the skeleton frame have satisfied each known joint movement of an exercise. In embodiments, a user can define custom exercises. In a custom exercise, the user can define the required movements for each joint, along with a sequence for each movement of the exercise, and then store the custom exercise. The repetition and counting module may track a user's movement during a workout session within the smart gym workout area and compare the user's movement with pre-defined exercises and custom exercises (known joint movements) to determine the particular exercise being performed. Once the exercise being performed is determined, the successful repetitions of the exercise may be counted.

For example, one repetition of a squat exercise may be to lower the hips with the thighs parallel to the floor, and return to a standing position. Thus, a known joint movement may be lowering the right hip joint 208A and the left hip joint 208B a predefined amount, along with joints 202A, 202B, 204A, 204B also lowering somewhat. Additionally, the camera may track movement of the joints 210A, 2108, 212A, and 2128 to ensure the knee joints maintain proper form and do not extend past the toes located near ankle joints 212A and 2128. In this example, a location of the toes may be captured by the camera or inferred by their proximity to the ankle joint. When an occurrence or instance of the current joint movements and the sequence of the movements by a user in the smart gym matches known joint movements stored as an exercise or a custom exercise, each occurrence or instance is counted as a repetition of the exercise. In embodiments, repetition counting for each exercise is different. For example, when a person is doing hammer curls, repetitions of each instance of the exercise may be determined based on a distance between the wrist joint 206A and shoulder joint 202A as well as an angle created at the elbow joint 204A during the exercise.

At block 316, a calorie counting module is executed. The calorie counting module may calculate the user's caloric expenditure based on the exercise being performed. In embodiments, the calculation of the number of calories burned by the user during exercise may be based on the user's profile and the particular weights, if any, being held by the user during exercise. At block 318, the captured information is synchronized to a cloud storage location. At block 320 the method 300 ends.

This process flow diagram is not intended to indicate that the blocks of the example method 300 are to be executed in any particular order, or that all of the blocks are to be included in every case. Further, any number of additional blocks not shown may be included within the example method 300, depending on the details of the specific implementation.

The processing unit may also derive the calories burned based on the a number of parameters, such as the (1) Weight of the user from User Profile and (2) the type of activity the user is doing (3) and the Intensity of the sports to determine the metabolic equivalent for a task (MET) to calculate the calories burnt. All information, including the calories burned, would be transmitted to a cloud storage location. The information can be viewed at any number of devices from the cloud storage location. For example, the data may be displayed in the user's phone. A person can use a mobile device to view fitness data such as what activities they completed, the total repetitions for each exercise, METs associated with each exercise, the duration of each exercise, the total duration of the workout, the calories burnt during each exercise and a total number of calories burned for the entire workout.

This fitness data may also be used as a training aid for professional athletes and coaches. In embodiments, virtual coaching may be enabled via the smart gym using haptic, auditory, visual feedback. For example, the known joint movement that is tracked during each exercise may be reviewed by coaches, physicians, and other professionals to derive training goals or correct issues observable during exercise. Algorithms can be used to analyze joint movement of a person. In embodiments, a person can receive immediate feedback on exercises performed in the smart gym on any mobile device via the cloud-based data. Moreover, historic data can be maintained for a person and can be compared with new data captured via the smart gym. In this manner, a person has the information necessary to improve or change techniques in real time instead of waiting for coaches to download and review the footage. Further, a person's workout can be changed instantaneously in response to metrics observed during a current workout in the smart gym. For example, consider a person with a workout that includes several lower body exercises. The person may have trouble completing repetitions of an exercise with the usual proper form (as indicated from the historic data) due to an injury or fatigue. However, the change in form may not be visible to humans. The change may be as small as a change squat depth of a few centimeters. The smart gym may alert the person or coach of the change in the person's typical movement. In response to this alert, immediate changes to the workout may be made to prevent any further injury or fatigue.

Given that the present techniques are based on movement capturing and analysis, they can be further extended in the future to include posture analysis as feedback to users to improve their workout. Additionally, in embodiments, data captured by the smart gym may be used to seed augmented-reality applications for users who want to virtually train with their favorite athletes, celebrities, or friends and family. In an augmented reality application, the cameras may capture the user during a workout and render the user in another environment. For example, while the user may physically be in a smart gym as described herein, the display may render the user in a second environment. In some cases, the second environment is a secondary workout space. The second environment may be a training environment with third parties, such as coaches or friends. In some examples, in an augmented reality application, the free weights, flooring, or other accessories used during the workout are enhanced by computer generated perceptual information. The perceptual information may include, for example, visual, auditory, haptic, somasensory, and olfactory information.

Figure 4:
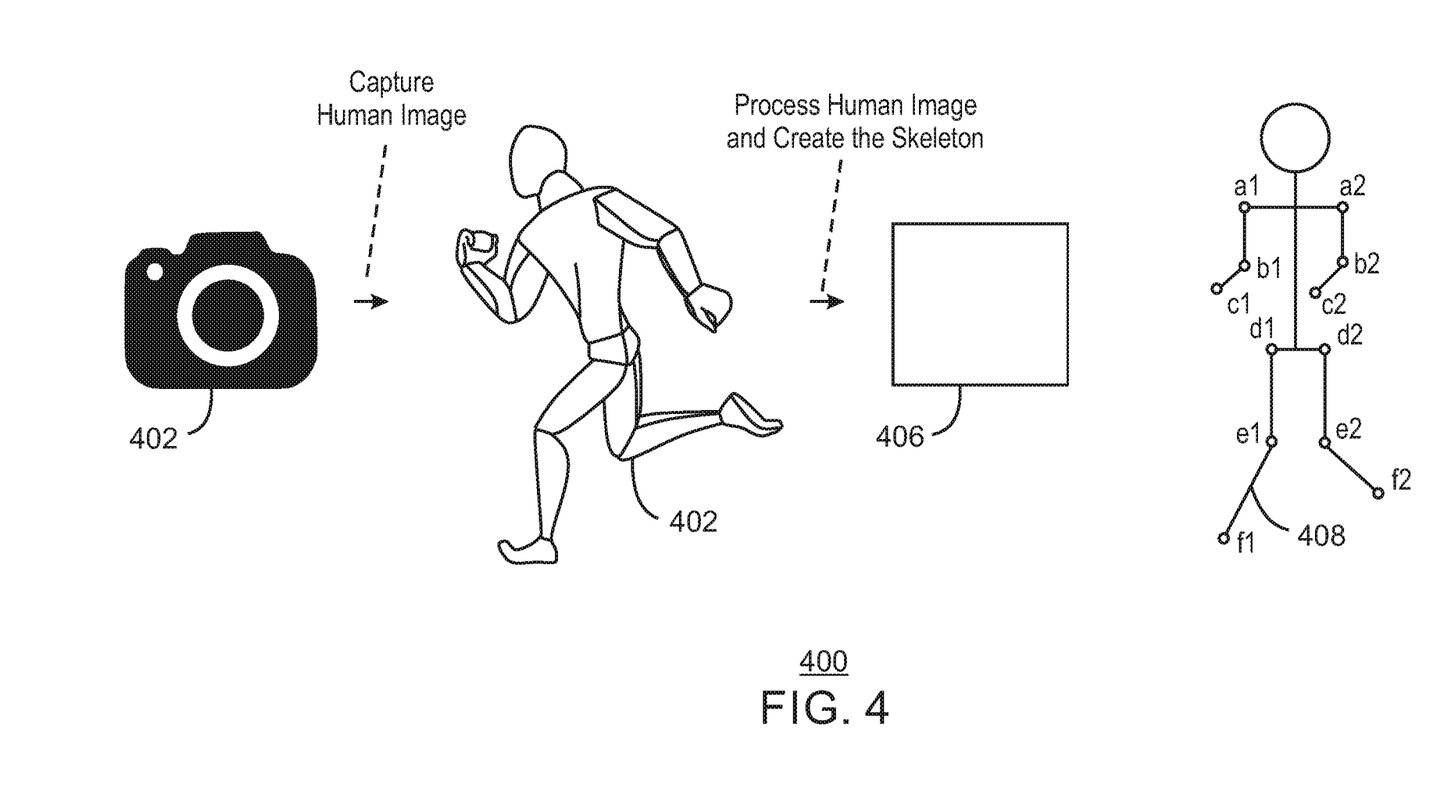
FIG. 4 is a block diagram of a system.

FIG. 4 is a block diagram of a system 400 that enables a smart gym. Similar to the example of FIG. 3, when a person 404 enters the free-weight platform and scan-in, his or her user profile such as name, age & weight will be captured. This information may be obtained from a stored profile, or the user can create a profile by entering this information into an application prior to the exercise. When movement is detected on a platform in the smart gym, the camera 402 will capture the person's 404 movement and the processing unit 406 will begin analysis. Images captured by the camera will be analyzed and matched against a database of exercises. The exercises may include pre-defined exercises and custom exercises. In embodiments, the exercises stored in the database may include exercises previously performed by the person.

The processing unit may also count repetitions of the exercise, as well as the total weight used during the exercise. During repetition counting, the camera 402 in the free weight area will capture the image of the person 404. The camera then sends the human image to the processing unit 406 to create the skeleton frame that corresponds to the person. In embodiments, the skeleton frame may have with 12 points or joints. Thus, the camera 402 will capture movement of the user 404 and processing unit 406 will begin analysis. The processing unit may derive a skeletal frame 408 of the user and track movement according to the movement of joints of the skeletal frame.

The diagram of FIG. 4 is not intended to indicate that the example system 400 is to include all of the components shown in FIG. 4. Rather, the example system 400 can be implemented using fewer or additional components not illustrated in FIG. 4 (e.g., additional cameras, neural networks, processing units, multiple people, multiple skeleton frames, etc.)

For ease of description, the present techniques describe exercise intensities according to a metabolic equivalent for task (MET). The MET is a unit that estimates the amount of energy used by the body during physical activity, as compared to resting metabolism. However, any measure of the rate at which a person expends energy relative to the weight of the person while performing activities can be used. The use of a person's weight when calculating this measure enables the measure to be standardized so that comparisons can be made between the fitness and activity levels between different people. In embodiments, the MET is standardized so it can apply to people of varying body weight and compare different activities. MET can be expressed in terms of oxygen use or kilocalories (what is commonly referred to as calories). Generally, the harder a person works during a given activity, the more oxygen is consumed and the higher the MET. Table 1 illustrates general MET ranges:

TABLE 1

| Under 3 MET | Light-intensity activities |
|---|---|
| 3 to 6 MET | Moderate-intensity aerobic physical activities, Burns 3.5 to 7 Calories per minute (kcal/min) |
| Over 6 MET | Vigorous-intensity aerobic physical activities |

Table 2 provides examples of moderate physical activity and vigorous physical activity:

TABLE 2

| Moderate physical activity | Vigorous physical activity |
|---|---|
| Walking | Running or jogging |
| On a treadmill at a speed of about 3 mph | Swimming laps |
| Water aerobics | Playing basketball or soccer |
| Ballroom dancing | Doing calisthenics like push- |
| Playing doubles tennis | ups and jumping jack |
|  | Playing tennis |

Table 3 provides exemplary MET values for a number of activities:

TABLE 3

| Activity | Specific Motion | Intensity | METs |
|---|---|---|---|
| Conditioning exercise | bicycling, stationary, RPM/Spin bike class | Moderate | 8.5 |
|  | calisthenics (e.g., pushups, sit ups, pull-ups, jumping jacks) | Vigorous | 8 |
|  | calisthenics (e.g., pushups, sit ups, pull-ups, lunges) | Moderate | 3.8 |
|  | calisthenics (e.g., sit-ups, abdominal crunches) | Light | 2.8 |
|  | Elliptical trainer | Moderate | 5 |
|  | resistance training (weight lifting, free weight, nautilus or universal), power lifting or body building | Vigorous | 6 |
|  | resistance (weight) training, squats, slow or explosive effort | Moderate | 5 |
|  | resistance (weight) training, multiple exercises, 8-15 repetitions at varied resistance | Light | 3.5 |
|  | rope skipping, general | Vigorous | 12.3 |
|  | rowing, stationary ergometer, general | Vigorous | 6 |
|  | rowing, stationary, general | Moderate | 4.8 |
| Running | jogging, general | Light | 7 |
|  | Running | Moderate | 8 |
|  | running, marathon | Vigorous | 13.3 |

TABLE 3-continued

| Activity | Specific Motion | Intensity | METs |
|---|---|---|---|
| Walking | walking for pleasure | Light | 3.5 |
| Water activities | swimming, breaststroke, general, training or competition | Vigorous | 10.3 |
|  | swimming, breaststroke, recreational | Light | 5.3 |
|  | swimming, leisurely, not lap swimming | Moderate | 6 |

The MET values may be stored in a database and used as a lookup table when calculating a total caloric expenditure. In embodiments, the total calories burned may be calculated as follows:

$$\text{Total caloric expenditure} = \frac{\text{Duration} * MET * 3.5 * \text{Weight}}{200}$$

Thus, the total calories burned during an exercise is the duration of the exercise in minutes, multiplied by the MET for the exercise, multiplied by 3.5, multiplied by the person's weight in kilograms; divided by 200. An intensity of a workout may be calculated as follows:

$$\text{Intensity} = \frac{\text{Duration}}{\text{Repetition Count}}$$

As indicated by the above equation, the intensity of an exercise may be calculated as the duration of the exercise in minutes divided by the repetition count for that exercise. Table 4 describes the intensity range for light, moderate, and vigorous activities:

TABLE 4

| Intensity Number | Activity |
|---|---|
| 0.51-1.0 | Light |
| 0.11-0.5 | Moderate |
| ≤0.1 | Vigorous |

At rest or sitting idly, the average person expends 1 MET, which equals 1 kilocalorie per kilogram of body weight times minutes of activity and 3.5 milliliters of oxygen per kilogram of body weight times minutes of activity. By using MET, the exertion required for different activities can be compared. At 2 MET a person uses using twice the calories per minute that a person can do at rest. The number of calories burned each minute depends on a person's body weight. A person who weighs more will burn more calories per minute.

The harder a person body works during any given activity the more oxygen is consumed and the higher the MET level. Tables 1-3 illustrate sample MET data. Generally, light intensity aerobic physical activities are considered to be under three METs. Moderate intensity aerobic physical activities are considered to be between three and six METs. Typically, activities over six METs are considered vigorous intensity aerobic physical activities. Generally, the weight training or resistance training that occurs during free weight exercises is considered moderate or vigorous intensity aerobic physical activity. As such, the resistance training that occurs during free weight exercises is interval to a fitness program. Thus, accurate tracking of free weight exercises is paramount to the training of athletes as well as individuals looking to get in better physical shape.

An intensity of a workout is determined by calculating the duration in minutes of the exercise divided by the number of repetitions of the exercise. For example, if a weight is lifted for seventy successful repetitions over ten minutes, the intensity would be as follows:

Intensity=10/70=0.14 (Moderate)

Consider the following use case. A user enters a smart gym and lifts dumbbells for 5 minutes during a lunch break. When the user scans-in to the smart gym, his or her user profile is captured or retrieved. In the present example, the user profile includes the following information: Name=Jane Doe, Age=30, Weight=52 kg. In embodiments, the user profile may also include sex, height, and any other physical information about the person. The person then ventures to the workout area and obtains a dumbbell and begins a workout on a smart gym platform. The person's activity is captured and analyzed to determine that the person is lifting a dumbbell. The platform is triggered by the user when the user steps on the platform. In response to the trigger, the platform captures a total weight of the user and the dumbbell as 57 kg. A processing unit of the smart gym system may calculate that the person is lifting 5 kg of dumbbell weight, since the person's weight is known to be 52 kg. A camera captures that the person did a total of 500 repetitions of lifting the dumbbell. The intensity of the workout may be calculated as Intensity of Workout =

Duration (in minutes)/repetition count = 5/50 = 0.1 (Vigorous)

So, Jane Doe's intensity of the five-minute workout in the smart gym is considered vigorous as found in Table 4. Referring to Table 3, the number for METs for the resistance training performed by Jane Doe is 6.

Total calories burnt =

Duration (in minuts) * (MET * 3.5 * weight in kg)/200 =

5 * (6 * 3.5 * 57)/200 = 5985/200 = 29.93 Calories burnt

In conclusion, Jane's 5 minutes dumbbell workout during lunch is as follows: She lifted 5 kg of dumbbell for 50 repetitions in 5 minutes which is vigorous. Her MET number is 6 and total calories burnt is 29.93

Figure 5:
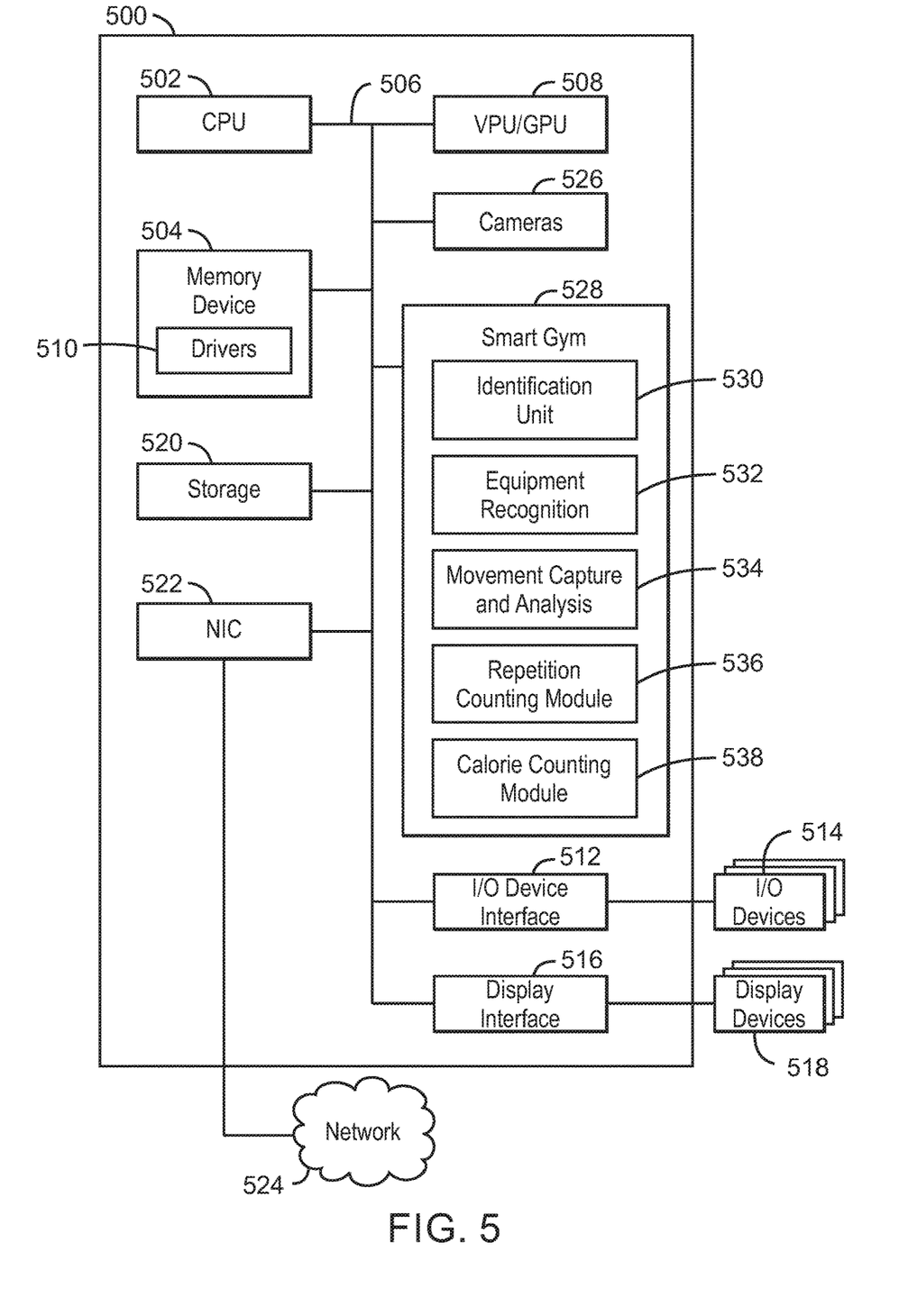
FIG. 5 is a block diagram is shown illustrating a computing device that enables a smart gym.

Referring now to FIG. 5, a block diagram is shown illustrating a computing device that enables a smart gym. The computing device 500 may be, for example, a laptop computer, desktop computer, tablet computer, mobile device, or wearable device, among others. The computing device 500 may include a central processing unit (CPU) 502 that is configured to execute stored instructions, as well as a memory device 504 that stores instructions that are executable by the CPU 502. The CPU 502 may be coupled to the memory device 504 by a bus 506. Additionally, the CPU 502 can be a single core processor, a multi-core processor, a computing cluster, or any number of other configurations. Furthermore, the computing device 500 may include more than one CPU 502. In some examples, the CPU 502 may be a system-on-chip (SoC) with a multi-core processor architecture. In some examples, the CPU 502 can be a specialized digital signal processor (DSP) used for image processing. The memory device 504 can include random access memory (RAM), read only memory (ROM), flash memory, or any other suitable memory systems. For example, the memory device 504 may include dynamic random-access memory (DRAM).

The computing device 500 may also include a vision processing unit or graphics processing unit (GPU) 508. As shown, the CPU 502 may be coupled through the bus 506 to the GPU 508. The GPU 508 may be configured to perform any number of graphics operations within the computing device 500. For example, the GPU 508 may be configured to render or manipulate graphics images, graphics frames, videos, or the like, to be displayed to a viewer of the computing device 500.

The CPU 502 may also be connected through the bus 506 to an input/output (I/O) device interface 512 configured to connect the computing device 500 to one or more I/O devices 514. The I/O devices 514 may include, for example, a keyboard and a pointing device, wherein the pointing device may include a touchpad or a touchscreen, among others. The I/O devices 514 may be built-in components of the computing device 500, or may be devices that are externally connected to the computing device 500. In some examples, the memory 504 may be communicatively coupled to I/O devices 514 through direct memory access (DMA).

The CPU 502 may also be linked through the bus 506 to a display interface 516 configured to connect the computing device 500 to a display device 516. The display devices 518 may include a display screen that is a built-in component of the computing device 500. The display devices 518 may also include a computer monitor, television, or projector, among others, that is internal to or externally connected to the computing device 500. The display device 516 may also include a head mounted display.

The computing device 500 also includes a storage device 520. The storage device 520 is a physical memory such as a hard drive, an optical drive, a thumbdrive, an array of drives, a solid-state drive, or any combinations thereof. The storage device 520 may also include remote storage drives.

The computing device 500 may also include a network interface controller (NIC) 522. The NIC 522 may be configured to connect the computing device 500 through the bus 506 to a network 524. The network 524 may be a wide area network (WAN), local area network (LAN), or the Internet, among others. In some examples, the device may communicate with other devices through a wireless technology. For example, the device may communicate with other devices via a wireless local area network connection. In some examples, the device may connect and communicate with other devices via Bluetooth® or similar technology.

The computing device 500 further includes a smart gym manager 528. The smart gym manager 528 may be configured to enable monitoring and tracking of free weight exercise or floor exercises along with a calculation of the number of calories burned during exercise. In particular, images captured by a plurality of cameras 526 may be processed with data captured by the cameras 526 such that a user can virtually train with a third-party, such as athletes, trainers, and coaches. The smart gym manager 528 includes an identification unit 530, an equipment recognition models 532, a movement capture and analysis module 534, a repetition counting module 536, and a calorie counting module 538.

The identification unit 530 may be configured to identify a person within the smart gym workout area. In particular, the identification unit may retrieve a user's profile data in response to the person entering the workout area. The person may self-identify prior to entering the workout area by providing all profile information or by providing authentication so that the identification unit 530 can retrieve the person's user profile from a data store. An equipment recognition module 532 may be configured to identify the particular equipment used by the person during a workout. For example, the equipment recognition module 532 may capture the weights of the person during exercise while holding weighted exercise accessories, such as dumbbells or more bills. The equipment used may be recognized by determining the weights of the equipment. The equipment used may also be recognized by capturing the equipment via the cameras 526 and using object identification to identify each weight. Moreover, each piece of equipment may include identifiers on the equipment that can be captured via the cameras 526 and identify via a matching process.

A movement capture and analysis module 534 may be configured to extract a skeleton frame corresponding to the person within the workout area. The skeleton frame may be expressed as a set of joints with relative locations. The movements of the skeleton frame of the person is tracked in a series of images captured while the person is exercising. A repetition counting module 536 may be configured to count a number of repetitions of an exercise that a person successfully completes. The particular exercise being performed may be initially determined by comparing the actual movements of the person to known joint movements stored in a database of the electronic device 500. In embodiments, custom exercises may be defined in the exercise database of the electronic device 500. When the current movements of the person engaging in exercise matches the known joint movements of an exercise stored in the exercise database, the repetition counting module 536 then counts each successful repetition of the exercise. A successful repetition of the exercise may include satisfying each particular movement in a particular sequence associated with the exercise. A calorie counting module 538 may be configured to calculate the caloric expenditure of the person during the exercise. MET values for various exercises may be stored in a lookup table. The total caloric expenditure may be calculated as the duration of the exercise in minutes, multiplied by the MET for the exercise, multiplied by 3.5, multiplied by the person's weight in kilograms; divided by 200.

The block diagram of FIG. 5 is not intended to indicate that the computing device 500 is to include all of the components shown in FIG. 5. Rather, the computing device 500 can include fewer or additional components not illustrated in FIG. 5, such as additional buffers, additional processors, and the like. The computing device 500 may include any number of additional components not shown in FIG. 5, depending on the details of the specific implementation. Furthermore, any of the functionalities of the smart gym manager 528, identification unit 530, equipment recognition module 532, movement capture and analysis module 534, repetition counting module 536, and calorie counting module 538 may be partially, or entirely, implemented in hardware and/or in the processor 502. For example, the functionality may be implemented with an application specific integrated circuit, in logic implemented in the processor 502, or in any other device. For example, the functionality of the smart gym manager 528 may be implemented with an application specific integrated circuit, in logic implemented in a processor, in logic implemented in a specialized graphics processing unit such as the VPU/GPU 508, or in any other device.

Figure 6:
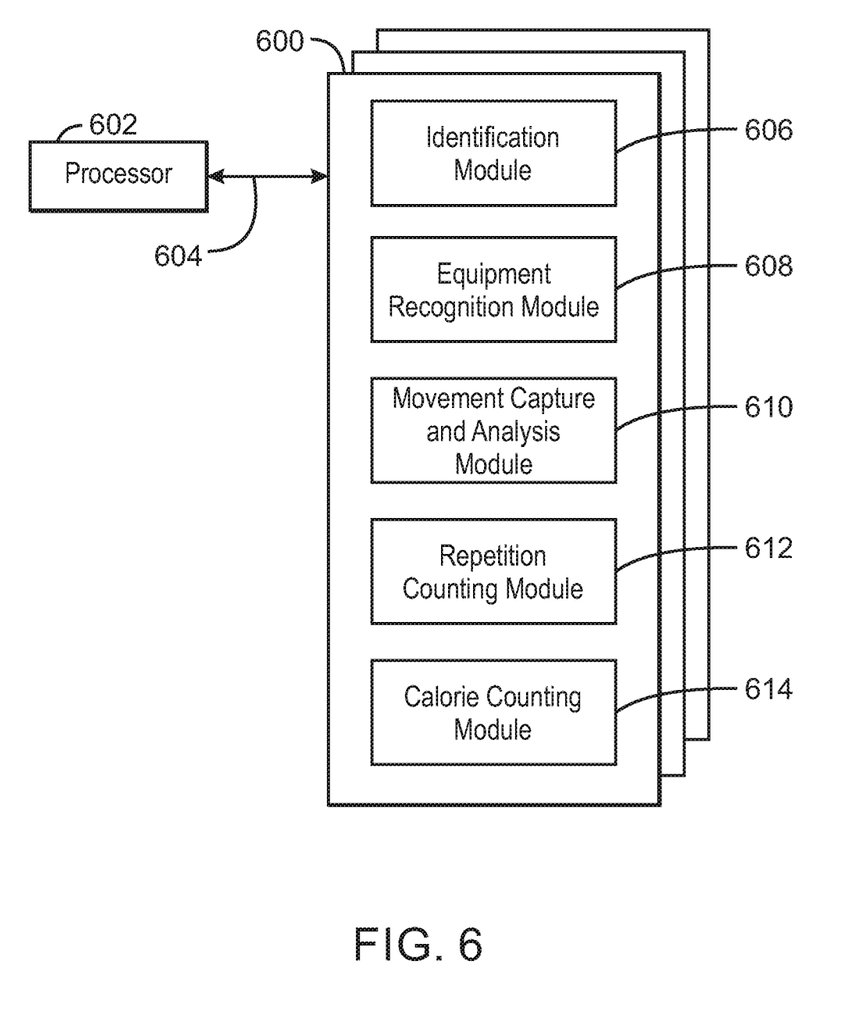
FIG. 6 is a block diagram showing computer readable media that stores code for enabling a smart gym.

FIG. 6 is a block diagram showing computer readable media 600 that stores code for enabling a smart gym. The computer readable media 600 may be accessed by a processor 602 over a computer bus 604. Furthermore, the computer readable medium 600 may include code configured to direct the processor 602 to perform the methods described herein. In some embodiments, the computer readable media 600 may be non-transitory computer readable media. In some examples, the computer readable media 600 may be storage media.

The various software components discussed herein may be stored on one or more computer readable media 600, as indicated in FIG. 6. For example, an identification module 606, equipment recognition module 608, a movement capture and analysis module 610, a repetition counting module 612, and a calorie counting module 614 may be stored on the computer readable media 600.

The identification module 606 may be configured to identify a person within the smart gym workout area. The equipment recognition module 608 may be configured to identify the particular equipment used by the person during a workout. The movement capture and analysis module 610 may be configured to extract a skeleton frame corresponding to the person within the workout area. The repetition counting module 612 may be configured to count a number of repetitions of an exercise that a person successfully completes. The calorie counting module 614 may be configured to calculate the caloric expenditure of the person during the exercise.

The block diagram of FIG. 6 is not intended to indicate that the computer readable media 600 is to include all of the components shown in FIG. 6. Further, the computer readable media 600 may include any number of additional components not shown in FIG. 6, depending on the details of the specific implementation.

Example 1 is an apparatus. The apparatus includes a platform, wherein the platform comprises at least a weight sensor; at least one camera, wherein the camera is configured to capture movements on the platform; a processor, wherein the processor is configured to: capture a person that has entered the platform area; derive a skeleton frame for the person in the platform area; track joint movements of the skeleton frame; identify one or more exercises performed by the tracked movement and count the number of repetitions performed; and calculate a caloric expenditure based on the number of repetitions performed, a weight of the person, and a weight used when performing the exercise.

Example 2 includes the apparatus of example 1, including or excluding optional features. In this example, an exercise is identified by comparing the joint movement to a known joint movement associated with the exercise. Optionally, the known joint movement is an average of the user's previous movements. Optionally, the known joint movement is reviewed to derive training goals.

Example 3 includes the apparatus of any one of examples 1 to 2, including or excluding optional features. In this example, the apparatus includes rendering the tracked movement of the skeleton frame on a display; and using augmented reality to place a third party on the screen with the rendering of the person.

Example 4 includes the apparatus of any one of examples 1 to 3, including or excluding optional features. In this example, the exercise is identified via machine leaning.

Example 5 includes the apparatus of any one of examples 1 to 4, including or excluding optional features. In this example, calculating the caloric expenditure is based on a metabolic equivalent for a task (MET).

Example 6 includes the apparatus of any one of examples 1 to 5, including or excluding optional features. In this example, virtual coaching is enabled via the smart gym with haptic, auditory, visual feedback.

Example 7 includes the apparatus of any one of examples 1 to 6, including or excluding optional features. In this example, in person coaching is enabled via the smart gym with post exercise playback or analysis.

Example 8 is a method. The method includes obtaining a user profile corresponding to a person in the workout area; extracting a skeleton frame from images captured of the person; tracking joint movements of the skeleton frame; identifying an exercise performed by the tracked movement and counting a number of repetitions of the exercise performed; and calculating a caloric expenditure based on the number of repetitions performed, a weight of the person, and a weight used when performing the exercise.

Example 9 includes the method of example 8, including or excluding optional features. In this example, an exercise is identified by comparing the joint movement to a known joint movement associated with the exercise. Optionally, the known joint movement is an average of the user's previous movements. Optionally, the known joint movement is reviewed to derive training goals.

Example 10 includes the method of any one of examples 8 to 9, including or excluding optional features. In this example, the method includes rendering the tracked movement of the skeleton frame on a display; and using augmented reality to place a third party on the screen with the rendering of the person.

Example 11 includes the method of any one of examples 8 to 10, including or excluding optional features. In this example, the exercise is identified via machine leaning.

Example 12 includes the method of any one of examples 8 to 11, including or excluding optional features. In this example, the caloric expenditure is based on a MET value obtained from a lookup table.

Example 13 includes the method of any one of examples 8 to 12, including or excluding optional features. In this example, virtual coaching is enabled via the smart gym with haptic, auditory, visual feedback.

Example 14 includes the method of any one of examples 8 to 13, including or excluding optional features. In this example, in person coaching is enabled via the smart gym with post exercise playback or analysis.

Example 15 is at least one computer readable medium that enables a smart gym having instructions stored therein that. The computer-readable medium includes instructions that direct the processor to obtain a user profile corresponding to a person in the workout area; extract a skeleton frame from images captured of the person; track joint movements of the skeleton frame; identify an exercise performed by the tracked movement and counting a number of repetitions of the exercise performed; and calculate a caloric expenditure based on the number of repetitions performed, a weight of the person, and a weight used when performing the exercise.

Example 16 includes the computer-readable medium of example 15, including or excluding optional features. In this example, an exercise is identified by comparing the joint movement to a known joint movement associated with the exercise. Optionally, the known joint movement is an average of the user's previous movements. Optionally, the known joint movement is reviewed to derive training goals.

Example 17 includes the computer-readable medium of any one of examples 15 to 16, including or excluding optional features. In this example, the computer-readable medium includes rendering the tracked movement of the skeleton frame on a display; and using augmented reality to place a third party on the screen with the rendering of the person.

Example 18 includes the computer-readable medium of any one of examples 15 to 17, including or excluding optional features. In this example, the exercise is identified via machine leaning.

Example 19 includes the computer-readable medium of any one of examples 15 to 18, including or excluding optional features. In this example, the caloric expenditure is based on a MET value obtained from a lookup table.

Not all components, features, structures, characteristics, etc. described and illustrated herein need be included in a particular aspect or aspects. If the specification states a component, feature, structure, or characteristic "may", "might", "can" or "could" be included, for example, that particular component, feature, structure, or characteristic is not required to be included. If the specification or claim refers to "a" or "an" element, that does not mean there is only one of the element. If the specification or claims refer to "an additional" element, that does not preclude there being more than one of the additional element.

It is to be noted that, although some aspects have been described in reference to particular implementations, other implementations are possible according to some aspects. Additionally, the arrangement and/or order of circuit elements or other features illustrated in the drawings and/or described herein need not be arranged in the particular way illustrated and described. Many other arrangements are possible according to some aspects.

In each system shown in a figure, the elements in some cases may each have a same reference number or a different reference number to suggest that the elements represented could be different and/or similar. However, an element may be flexible enough to have different implementations and work with some or all of the systems shown or described herein. The various elements shown in the figures may be the same or different. Which one is referred to as a first element and which is called a second element is arbitrary.

It is to be understood that specifics in the aforementioned examples may be used anywhere in one or more aspects. For instance, all optional features of the computing device described above may also be implemented with respect to either of the methods or the computer-readable medium described herein. Furthermore, although flow diagrams and/or state diagrams may have been used herein to describe aspects, the techniques are not limited to those diagrams or to corresponding descriptions herein. For example, flow need not move through each illustrated box or state or in exactly the same order as illustrated and described herein.

The present techniques are not restricted to the particular details listed herein. Indeed, those skilled in the art having the benefit of this disclosure will appreciate that many other variations from the foregoing description and drawings may be made within the scope of the present techniques. Accordingly, it is the following claims including any amendments thereto that define the scope of the present techniques.

What is claimed is:

1. An apparatus, comprising:
    a platform, wherein the platform includes at least a weight sensor;
    at least one camera, wherein the camera is configured to capture movements on the platform;
    instructions;
    a processor, wherein the processor is configured by the instructions to:
        capture a person that has entered the platform area;

derive a skeleton frame for the person in the platform area;
track joint movements of the skeleton frame;
identify one or more exercises performed by the tracked movement and count the number of repetitions performed; and
calculate a caloric expenditure based on the number of repetitions performed, a weight of the person, and a weight used when performing the one or more exercises.

2. The apparatus of claim 1, wherein the processor identifies the one or more exercises by comparing the joint movement to a known joint movement associated with the exercise.

3. The apparatus of claim 2, wherein the known joint movement is an average of the user's previous movements.

4. The apparatus of claim 2, wherein the processor is to review the known joint movement to derive training goals.

5. The apparatus of claim 1, wherein the processor is to:
cause the tracked movement of the skeleton frame to be rendered on a display; and
use augmented reality to place a third party on the screen with the rendering of the person.

6. The apparatus of claim 1, wherein the exercise is identified via machine leaning.

7. The apparatus of claim 1, wherein the processor is to calculate the caloric expenditure based on a metabolic equivalent for a task (MET).

8. The apparatus of claim 1, wherein virtual coaching is enabled via the smart gym with haptic, auditory, visual feedback.

9. The apparatus of claim 1, wherein in person coaching is enabled via the smart gym with post exercise playback or analysis.

10. A method, comprising:
obtaining a user profile corresponding to a person in a workout area;
extracting a skeleton frame from images captured of the person;
tracking joint movements of the skeleton frame;
identifying an exercise performed by the tracked movement and counting a number of repetitions of the exercise performed; and
calculating a caloric expenditure based on the number of repetitions performed, a weight of the person, and a weight used when performing the exercise.

11. The method of claim 10, wherein the exercise is identified by comparing the joint movement to a known joint movement associated with the exercise.

12. The method of claim 11, wherein the known joint movement is an average of the user's previous movements.

13. The method of claim 11, wherein the known joint movement is reviewed to derive training goals.

14. The method of claim 10, comprising:
rendering the tracked movement of the skeleton frame on a display; and
using augmented reality to place a third party on the screen with the rendering of the person.

15. The method of claim 10, wherein the exercise is identified via machine leaning.

16. The method of claim 10, wherein the caloric expenditure is based on a MET value obtained from a lookup table.

17. The method of claim 10, wherein virtual coaching is enabled via the smart gym with haptic, auditory, visual feedback.

18. The method of claim 10, wherein in person coaching is enabled via the smart gym with post exercise playback or analysis.

19. At least one computer readable medium that enables a smart gym, the at least one computer readable medium comprising instructions stored therein that, in response to being executed on a computing device, cause the computing device to:
obtain a user profile corresponding to a person in the workout area;
extract a skeleton frame from images captured of the person;
track joint movements of the skeleton frame;
identify an exercise performed by the tracked movement and count a number of repetitions of the exercise performed; and
calculate a caloric expenditure based on the number of repetitions performed, a weight of the person, and a weight used when performing the exercise.

20. The computer readable medium of claim 19, wherein the exercise is identified by comparing the joint movement to a known joint movement associated with the exercise.

21. The computer readable medium of claim 20, wherein the known joint movement is an average of the user's previous movements.

22. The computer readable medium of claim 20, wherein the known joint movement is reviewed to derive training goals.

23. The computer readable medium of claim 19, wherein the instructions cause the computing device to:
render the tracked movement of the skeleton frame on a display; and
use augmented reality to place a third party on the screen with the rendering of the person.

24. The computer readable medium of claim 19, wherein the exercise is identified via machine leaning.

25. The computer readable medium of claim 19, wherein the caloric expenditure is based on a MET value obtained from a lookup table.

* * * * *